(12) United States Patent
Pytela et al.

(10) Patent No.: US 10,377,814 B2
(45) Date of Patent: *Aug. 13, 2019

(54) FUSION PARTNER FOR PRODUCTION OF MONOCLONAL RABBIT ANTIBODIES

(71) Applicant: EPITOMICS, Inc., Burlingame, CA (US)

(72) Inventors: Robert Pytela, San Francisco, CA (US); Weimin Zhu, San Francisco, CA (US); Yaohuang Ke, San Francisco, CA (US); Qi Qian, San Francisco, CA (US); Harry C. Au, San Francisco, CA (US)

(73) Assignee: EPITOMICS, INC., Burlingame, CA (US)

( * ) Notice: Subject to any disclaimer, the term of this patent is extended or adjusted under 35 U.S.C. 154(b) by 498 days.

This patent is subject to a terminal disclaimer.

(21) Appl. No.: 15/089,135

(22) Filed: Apr. 1, 2016

(65) Prior Publication Data

US 2016/0207982 A1 Jul. 21, 2016

Related U.S. Application Data

(63) Continuation of application No. 13/732,912, filed on Jan. 2, 2013, now Pat. No. 9,328,333, which is a continuation of application No. 13/274,946, filed on Oct. 17, 2011, now Pat. No. 8,367,408, which is a continuation of application No. 12/755,212, filed on Apr. 6, 2010, now Pat. No. 8,062,867, which is a continuation of application No. 12/196,234, filed on Aug. 21, 2008, now Pat. No. 7,732,168, which is a continuation of application No. 11/476,277, filed on Jun. 27, 2006, now Pat. No. 7,429,487.

(60) Provisional application No. 60/697,014, filed on Jul. 5, 2005.

(51) Int. Cl.
*C07K 16/00* (2006.01)
*C12N 5/16* (2006.01)
*C12P 21/00* (2006.01)

(52) U.S. Cl.
CPC .............. *C07K 16/00* (2013.01); *C12N 5/163* (2013.01); *C12P 21/005* (2013.01); *C07K 2317/24* (2013.01); *C07K 2317/622* (2013.01)

(58) Field of Classification Search
None
See application file for complete search history.

(56) References Cited

U.S. PATENT DOCUMENTS 5,675,063 A  10/1997  Knight

OTHER PUBLICATIONS

Babcook, et al., "A novel strategy for generating monoclonal antibodies from single, isolated lymphocytes producing antibodies of defined specificities", Proc Natl Acad Sci, 1996, 93:7843-8.

(Continued)

*Primary Examiner* — Sharon X Wen
(74) *Attorney, Agent, or Firm* — James S. Keddie; Bozicevic, Field & Francis LLP

(57) ABSTRACT

The invention provides a rabbit-derived immortal B-lymphocyte capable of fusion with a rabbit splenocyte to produce a hybrid cell that produces an antibody. The immortal B-lymphocyte does not detectably express endogenous immunoglobulin heavy chain and may contain, in certain embodiments, an altered immunoglobulin heavy chain-encoding gene. A hybridoma resulting from fusion between the subject immortal B-lymphocyte and a rabbit antibody-producing cell is provided, as is a method of using that hybridoma to produce an antibody. The subject invention finds use in a variety of different diagnostic, therapeutic and research applications.

20 Claims, 5 Drawing Sheets
Specification includes a Sequence Listing.

(56) References Cited

OTHER PUBLICATIONS

Borras, et al., "Generic approach for the generation of stable humanized single-chain Fv fragments from rabbit monoclonal antibodies", J Biol Chem, 2010, 285:9054-66.

Borup-Christensen, et al., "Human-human hybridomas generated with lymphocytes from patients with colorectal cancer", Cancer Detect Prev Suppl., 1987, 1:207-15.

Carson, et al., "Human lymphocyte hybridomas and monoclonal antibodies", Adv Immunol, 1986, 38:275-311.

Clark, "Monoclonal antibodies derived from hybrid myelomas", Ric Clin Lab, 1981, 11:195-203.

Kawahara, et al., "A new human fusion partner, HK-128, for making human-human hybridomas producing monoclonal IgG antibodies", Cytotechnology, 1990, 4:139-43.

Liguori, et al., "Recombinant human interleukin-6 enhances the immunoglobulin secretion of a rabbit-rabbit hybridoma", 2001, 20:189-98.

Posner, et al., "The construction and use of a human-mouse myeloma analogue suitable for the routine production of hybridomas secreting human monoclonal antibodies", Hybridoma, 1987, 6:611-25.

Raybould, et al., "Production of stable rabbit-mouse hybridomas that secrete rabbit mAb of defined specificity", Science, 1988, 240:1788-90.

Rief et al., "Production and Characterization of a Rabbit Monoclonal Antibody Against Human CDC25C Phosphatase", HYBRIDOMA(1998), 17(4), pp. 389-394.

Rossi, et al., "Rabbit monoclonal antibodies: a comparative study between a novel category of immunoreagents and the corresponding mouse monoclonal antibodies", Am J Clin Pathol, 2005, 124:295-302.

Spieker-Polet et al., "Rabbit Monoclonal Antibodies: Generating a Fusion Partner to Produce Rabbit-Rabbit Hybridomas", Proc. Natl. Acad. Sci. USA. (1995), 26:92(20); pp. 9348-9352.

Verbanac, et al., "Production of stable rabbit-mouse heterohybridomas: characterization of a rabbit monoclonal antibody recognizing a 180 kDa human lymphocyte membrane antigen", Hybridoma, 1993, 12:285-95.

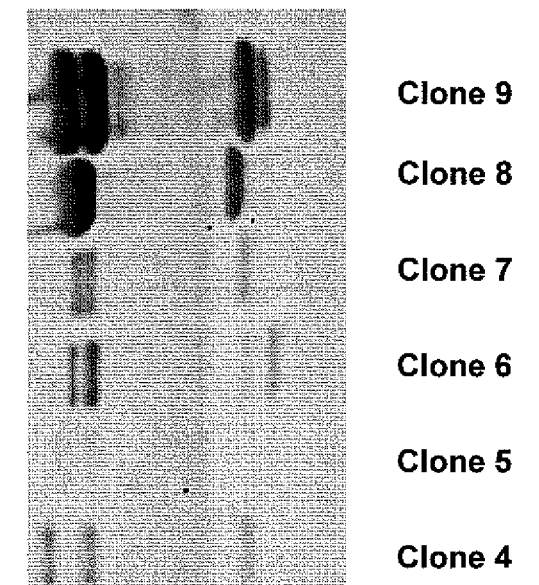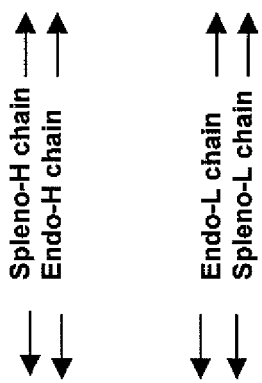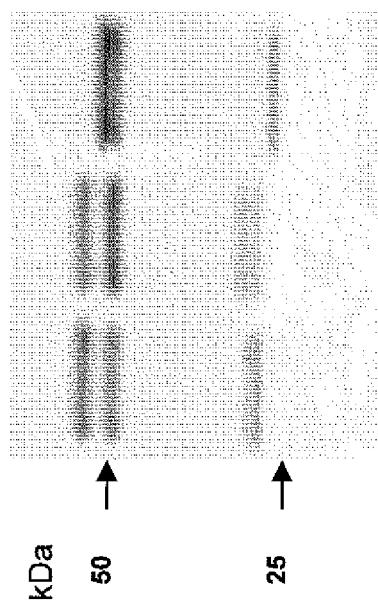
Fig. 1

```
GTCCAGTGTCAGCAGCTGGAGCAGTCCGGAGGAGGAAGGAGGCCTGGTCAAGCCT      60
 V  Q  C  Q  L  E  Q  S  G  G  G  G  A  E  G  G  L  V  K  P
GGGGATCCCTGGAACTCTGCTTGCAAAGCCTCTGGATTCTCCCTCAGTAGTAGCTACTGC  120
 G  G  S  L  E  L  C  C  K  A  S  G  F  S  L  S  S  S  Y  C
ATATGTTGGGTCCGCCAGGCTCCAGGGAAGGGCTGGAGTGGATCGGATGCATTTATGCT   180
 I  C  W  V  R  Q  A  P  G  K  G  L  E  W  I  G  C  I  Y  A
GGTAGTAGTGGTAGCACTTACTACGCGAGCTGGGTGAATGGCCGATTCACTCTCTCCAGA  240
 G  S  S  G  S  T  Y  Y  A  S  W  V  N  G  R  F  T  L  S  R
GACATTGACCAGAGCACAGGTTGCCTACAACTGAACAGTCTGACAGCCGCGGACACGGCC  300
 D  I  D  Q  S  T  G  C  L  Q  L  N  S  L  T  A  A  D  T  A
ATGTATTACTGTGCGAGAGCCCCCTATAGTAGTGGCTGGGTCCTCTACTTTAACTTGTGG  360
 M  Y  Y  C  A  R  A  P  Y  S  S  G  W  V  L  Y  F  N  L  W
GGCCCAGGCACCCTGGTCACCGTCTCCTCCG                                392
 G  P  G  T  L  V  T  V  S  S  G
```

Fig. 2

SEQUENCE LISTING

<160> NUMBER OF SEQ ID NOS: 2

<210> SEQ ID NO 1
<211> LENGTH: 391
<212> TYPE: DNA
<213> ORGANISM: Oryctolagus cuniculus

<400> SEQUENCE: 1

```
gtccagtgtc agcagctgga gcagtccgga ggaggagccg aaggaggcct ggtcaagcct      60
gggggatccc tggaactctg ctgcaaagcc tctggattct ccctcagtag tagctactgc     120
atatgttggg tccgccaggc tccagggaag gggctggagt ggatcggatg catttatgct     180
ggtagtagtg gtagcactta ctacgcgagc tgggtgaatg gccgattcac tctctccaga     240
gacattgacc agagcacagg ttgcctacaa ctgaacagtc tgacagccgc ggacacggcc     300
atgtattact gtgcgagagc cccctatagt agtggctggg tcctctactt taacttgtgg     360
ggcccaggca ccctggtcac cgtctcctcc g                                    391
```

<210> SEQ ID NO 2
<211> LENGTH: 131
<212> TYPE: PRT
<213> ORGANISM: Oryctolagus cuniculus

<400> SEQUENCE: 2

```
Val Gln Cys Gln Gln Leu Glu Gln Ser Gly Gly Gly Ala Glu Gly Gly
1               5                   10                  15

Leu Val Lys Pro Gly Gly Ser Leu Glu Leu Cys Cys Lys Ala Ser Gly
            20                  25                  30

Phe Ser Leu Ser Ser Ser Tyr Cys Ile Cys Trp Val Arg Gln Ala Pro
        35                  40                  45

Gly Lys Gly Leu Glu Trp Ile Gly Cys Ile Tyr Ala Gly Ser Ser Gly
    50                  55                  60

Ser Thr Tyr Tyr Ala Ser Trp Val Asn Gly Arg Phe Thr Leu Ser Arg
65                  70                  75                  80

Asp Ile Asp Gln Ser Thr Gly Cys Leu Gln Leu Asn Ser Leu Thr Ala
                85                  90                  95

Ala Asp Thr Ala Met Tyr Tyr Cys Ala Arg Ala Pro Tyr Ser Ser Gly
            100                 105                 110

Trp Val Leu Tyr Phe Asn Leu Trp Gly Pro Gly Thr Leu Val Thr Val
        115                 120                 125

Ser Ser Gly
    130
```

FUSION PARTNER FOR PRODUCTION OF MONOCLONAL RABBIT ANTIBODIES

INTRODUCTION

Field of the Invention

The invention relates to a fusion partner for the production of rabbit monoclonal antibodies.

Background of the Invention

It has long been recognized that rabbit antibodies have favorable properties compared to mouse antibodies. First, rabbits are known to produce antibodies to many antigens that are poorly immunogenic in mice (e.g., Norrby et al., Proc. Natl. Acad. Sci. 1987 84:6572-6; Raybould & Takahashi, Science 1988 240:1788-90 and Weller et al., Development 1987; 100:351-63). For example, Bystryn et al (Hybridoma 1982 1:465-72) directly compared rabbit and mouse antibodies directed against human melanoma cells and showed that they recognize different epitopes. Second, rabbit antibodies are generally of high affinity. Third, because most monoclonal antibodies are generated in mice and rats, relatively few monoclonal antibodies are available that react with mouse or rat immunogens. In spite of these advantages, until recently it has been impossible to raise monoclonal antibodies in the rabbit. Monoclonal antibodies are predominantly produced by using the hybridoma technology originally developed by Koehler and Milstein (Nature 1975 256:495-7). This method involves immortalization of antibody-producing lymphocytes by fusion with myeloma cells. Since myeloma-like tumors are unknown in the rabbit, it has been impossible to use this approach for producing rabbit monoclonal antibodies. Attempts have been made to use mouse myeloma cell lines as fusion partners (e.g., Raybould & Takahashi, 1988, supra), or to use in vitro-transformed lymphoid cell lines from rabbits, but in all cases these approaches were hampered by the instability of the resulting hybridomas.

A novel approach was taken by K. Knight and colleagues (Spieker-Polet et al., Proc. Natl. Acad. Sci. 1995 92:9348-52), who succeeded in producing a myeloma-like tumor in transgenic rabbits expressing oncogenes under the control of the immunoglobulin heavy and light chain enhancers. They isolated a plasmacytoma cell line, termed 240E-1, from these tumors, and showed that fusions of 240E-1 cells with rabbit lymphocytes produced hybridomas. Hybridomas were produced from lymphocytes of rabbits immunized using plasma proteins or whole cells, and were shown to secrete IgG antibodies.

An improved fusion partner cell line for the production of monoclonal antibodies from rabbits is provided.

Literature

References of interest include Spieker-Polet et al., Proc. Natl. Acad. Sci. 1995 92:9348-52; Rief et al., Hybridoma 1998 17:389-394; Liguori et al., 2001 Hybridoma 2001 20:189-98 and U.S. Pat. No. 5,675,063.

SUMMARY OF THE INVENTION

The invention provides a rabbit-derived immortal B-lymphocyte capable of fusion with a rabbit splenocyte to produce a hybrid cell that produces an antibody. The immortal B-lymphocyte does not detectably express endogenous immunoglobulin heavy chain and may contain, in certain embodiments, an altered immunoglobulin heavy chain-encoding gene. A hybridoma resulting from fusion between the subject immortal B-lymphocyte and a rabbit antibody-producing cell is provided, as is a method of using that hybridoma to produce an antibody. The subject invention finds use in a variety of different diagnostic, therapeutic and research applications.

BRIEF DESCRIPTION OF THE DRAWINGS

FIG. 1 is two panels showing that hybridoma cell lines derived from the 240E-W fusion partner express variable amounts of an endogenous Ig heavy chain. Hybridoma lines derived from 240E-W secrete endogenous Ig heavy and light chains. IgG proteins secreted by nine different rabbit hybridoma lines were analyzed by SDS-PAGE (reducing conditions) after purification by protein G affinity chromatography (left-hand panel) or by western blotting with goat-anti rabbit IgG antibodies (right-hand panel). The protein bands at approx. 50 kDa correspond to Ig heavy chains, the bands at approx. 25 kDa to Ig kappa light chains. Each clone produces a spleen-derived heavy chain (spleno-H chain) of slightly variable size (upper band), and a 240E-W-derived heavy chain (endo-H chain) of constant size (lower band).

FIG. 2 shows the amino acid sequence of the variable domain of the endogenous heavy chain of 240E-W (SEQ ID NO:1), and its encoding cDNA (SEQ ID NO:2). The endo-IgH cDNA was amplified by RT-PCR from 240E-W cell mRNA, using primers corresponding to the 5' end of the rabbit vH segment, combined with primers corresponding to the 3' end of the rabbit IgG constant domain. The sequence of the mature vH domain is shown, beginning with the first amino acid following the signal peptide.

FIG. 5. Rabbit hybridoma cell lines derived from the improved fusion partner cell line, 240E-W2, secrete only one type of Ig heavy chain, and do not produce the endogenous heavy chain present in 240E-W cells. Supernatants from five different 240E-W2-derived hybridoma clones (lanes 1-3, 5, and 6), and a supernatant from a 240E-W-derived hybridoma (lane 4) were analyzed by SDS-PAGE followed by western blotting with goat-anti rabbit IgG antibodies. Note that the endo-IgH chain (lower band in lane 4) is not detected in any of the 240E-W2-derived hybridoma supernatants, confirming that the endo-IgH gene has indeed been removed or inactivated in the 240E-W2 fusion partner cell line.

DEFINITIONS

Figure 3:
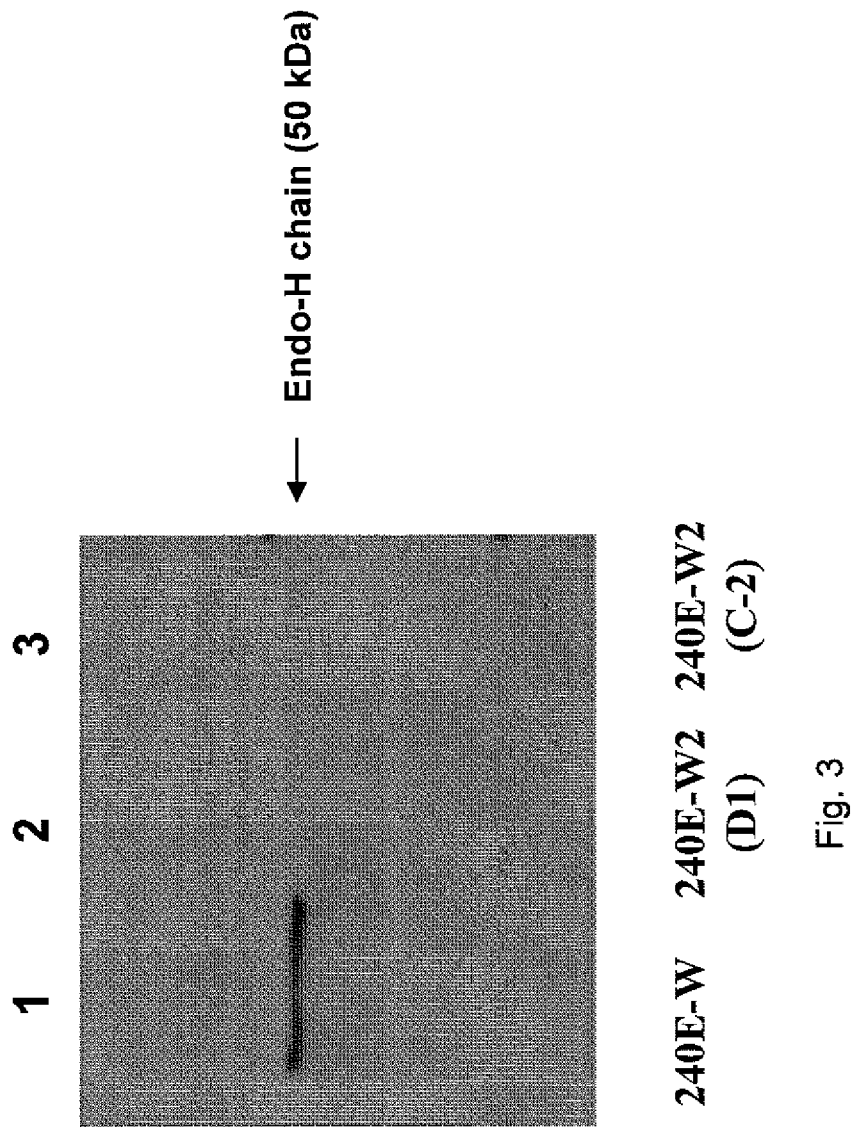
FIG. 3 is a western blot showing that endo-IgH protein was not detected in the 240E-W2 line, while it was strongly detected in the 240E-W. 240E-W2 cell lines do not express detectable endogenous Ig heavy chain protein (endo-H chain). SDS-PAGE analysis of cell lysates prepared from the parent fusion partner cell line, 240E-W (lane 1), and two different 240E-W2 clones (lanes 2 and 3). Ig heavy chains were detected by western blotting with goat-anti rabbit IgG antibodies. The 240E-W2 clones are derived from a hybridoma line that was subcloned and selected for the absence of endo-H protein (see text). Note that Ig heavy chain protein (50 kDa) is detected in the parent line 240E-W, but not in the 240E-W2 clones.

The terms "antibody" and "immunoglobulin" are used interchangeably herein. These terms are well understood by those in the field, and refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized immunoglobulin polypeptides include the kappa and lambda light chains and the alpha, gamma ($IgG_1$, $IgG_2$, $IgG_3$, $IgG_4$), delta, epsilon and mu heavy chains or equivalents in other species. Full-length immunoglobulin "light chains" (of about 25 kDa or about 214 amino acids) comprise a variable region of about 110 amino acids at the $NH_2$-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the terms are Fab', Fv, $F(ab')_2$, and or other antibody fragments that retain specific binding to antigen.

Antibodies may exist in a variety of other forms including, for example, Fv, Fab, and $(Fab')_2$, as well as bi-functional (i.e. bi-specific) hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988); Bird et al., Science, 242, 423-426 (1988); see Hood et al., "Immunology", Benjamin, N.Y., 2nd ed. (1984), and Hunkapiller and Hood, Nature, 323, 15-16 (1986)).

An immunoglobulin light or heavy chain variable region consists of a "framework" region interrupted by three hypervariable regions, also called "complementarity determining regions" or CDRs. The extent of the framework region and CDRs have been precisely defined (see, "Sequences of Proteins of Immunological Interest," E. Kabat et al., U.S. Department of Health and Human Services, (1983)). The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen.

Chimeric antibodies are antibodies whose light and heavy chain genes have been constructed, typically by genetic engineering, from antibody variable and constant region genes belonging to different species. For example, the variable segments of the genes from a rabbit monoclonal antibody may be joined to human constant segments, such as gamma 1 and gamma 3. An example of a therapeutic chimeric antibody is a hybrid protein composed of the variable or antigen-binding domain from a rabbit antibody and the constant or effector domain from a human antibody (e.g., the anti-Tac chimeric antibody made by the cells of A.T.C.C. deposit Accession No. CRL 9688), although other mammalian species may be used.

As used herein, unless otherwise indicated or clear from the context, antibody domains, regions and fragments are accorded standard definitions as are well known in the art. See, e.g., Abbas, A. K., et al., (1991) Cellular and Molecular Immunology, W. B. Saunders Company, Philadelphia, Pa.

As used herein, the terms "determining," "measuring," and "assessing," and "assaying" are used interchangeably and include both quantitative and qualitative determinations.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, (3-galactosidase, luciferase, etc.; and the like.

As used herein the term "isolated," when used in the context of an isolated antibody, refers to an antibody of interest that is at least 60% free, at least 75% free, at least 90% free, at least 95% free, at least 98% free, and even at least 99% free from other components with which the antibody is associated with prior to purification.

A "coding sequence" or a sequence that "encodes" a selected polypeptide, is a nucleic acid molecule which is transcribed (in the case of DNA) and translated (in the case of mRNA) into a polypeptide, for example, in vivo when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences that are immunologically identifiable with a polypeptide encoded by the sequence.

"Operably linked" refers to an arrangement of elements wherein the components so described are configured so as to perform their usual function. Thus, a given signal peptide that is operably linked to a polypeptide directs the secretion of the polypeptide from a cell. In the case of a promoter, a promoter that is operably linked to a coding sequence will direct the expression of a coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

By "nucleic acid construct" it is meant a nucleic acid sequence that has been constructed to comprise one or more functional units not found together in nature. Examples include circular, linear, double-stranded, extrachromosomal DNA molecules (plasmids), cosmids (plasmids containing COS sequences from lambda phage), viral genomes comprising non-native nucleic acid sequences, and the like.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells, which can be accomplished by genomic integration of all or a portion of the vector, or transient or inheritable maintenance of the vector as an extrachromosomal element. Thus, the term includes cloning, and expression vehicles, as well as integrating vectors.

An "expression cassette" comprises any nucleic acid construct capable of directing the expression of a gene/coding sequence of interest, which is operably linked to a promoter of the expression cassette. Such cassettes can be constructed into a "vector," "vector construct," "expression vector," or "gene transfer vector," in order to transfer the expression cassette into target cells. Thus, the term includes cloning and expression vehicles, as well as viral vectors.

The term "specific binding" refers to the ability of an antibody to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold).

In certain embodiments, the affinity between a capture agent and analyte when they are specifically bound in a capture agent/analyte complex is characterized by a $K_D$ (dissociation constant) of less than $10^{-6}$M, less than $10^{-7}$ M, less than $10^{-8}$ M, less than $10^{-9}$ M, less than $10^{-9}$ M, less than $10^{-11}$ M, or less than about $10^{-12}$ M or less.

A polynucleotide is "derived from" a particular cell if the polynucleotide was obtained from the cell. A polynucleotide may also be "derived from" a particular cell if the polynucleotide was obtained from the progeny of the cell, as long as the polynucleotide was present in the original cell. As such, a single cell may be isolated and cultured, e.g. in vitro, to form a cell culture. A nucleotide isolated from the cell culture is "derived from" the single cell, as long as the nucleic acid was present in the isolated single cell.

A "rabbit-derived" cell is a progenitor of a cell obtained from a rabbit.

Before the present subject invention is described further, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an antibody" includes a plurality of such antibodies and reference to "a variable domain" includes reference to one or more variable domains and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The invention provides a rabbit-derived immortal B-lymphocyte capable of fusion with a rabbit splenocyte to produce a hybrid cell that produces an antibody. The immortal B-lymphocyte does not detectably express endogenous immunoglobulin heavy chain and may contain, in certain embodiments, an altered immunoglobulin heavy chain-encoding gene. A hybridoma resulting from fusion between the subject immortal B-lymphocyte and a rabbit antibody-producing cell is provided, as is a method of using that hybridoma to produce an antibody. The subject invention finds use in a variety of different diagnostic, therapeutic and research applications.

In further describing the subject invention, the immortal B-lymphocytes of the invention will be described first, followed by a review of the methods and applications in which the subject cells find use.

Immortal B-Lymphocytes Having Undetectable Immunoglobulin Heavy Chain Expression As mentioned above, the invention provides an immortal rabbit B-lymphocyte fusion partner having undetectable endogenous immunoglobulin heavy chain expression. The fusion partner cell may be fused with an antibody-producing cell from a rabbit, e.g., an immunized rabbit, to produce a hybridoma cell. The hybridoma cell, like the fusion partner, produces no detectable endogenous immunoglobulin heavy chain, where "endogenous" immunoglobulin heavy chain refers to the immunoglobulin heavy chain encoded by the parental fusion partner cell.

In certain embodiments, therefore, the subject fusion partner may contain an altered, non-functional, immunoglobulin heavy chain gene (e.g., a heavy chain gene containing an insertion, deletion, inversion or point mutation in the coding sequence or non-coding sequence such as in the promoter or an intron of the heavy chain gene, for example; or the heavy chain gene that may have been lost due to partial or complete chromosome loss). In certain embodiments, the endogenous immunoglobulin heavy chain polypeptide has the sequence shown in FIG. 2, or a variant thereof that is at least 95%, e.g., at least 96%, at least 97%, at least 98%, or at least 99% identical to that sequence and may be encoded by the cDNA shown in FIG. 2 or a cDNA that hybridizes to and/or is at least 95%, e.g., at least 96%, at least 97%, at least 98%, or at least 99% identical to that sequence. Immunoglobulin heavy chain gene expression may be detected at the cDNA or protein level by RT-PCR or immunoblotting, for example.

In certain embodiments, a subject immortal rabbit B-lymphocyte fusion partner (or hybridoma thereof) may also exhibit undetectable immunoglobulin light chain expression.

The fusion partner cell of the invention is further characterized in that it is capable of fusion with a rabbit splenocyte at a highly efficient rate (in the range of 40%-80%, or, in certain embodiments, at least 80%), using methods essentially as described in Spieker-Polet et al. (Proc. Natl. Acad. Sci. 1995 92:9348-52), but with the modifications described in example 1. In other words, in a method that involves fusing spleen cells of an immunized rabbit with the subject fusion partner at a cell ratio of 2:1 (spleen cells:fusion partner cells), plating of those cells in a 96-well microtiter plate at approximately $2\times10^5$ spleen cells per well and selecting of HAT-resistant cells, results in approximately 40%-80%, or, in certain embodiments, at least 80% or at least 90%) of the wells of the microtiter plate contain a hybridoma colony.

Further to the above, the subject fusion partner is also characterized by an ability to produce hybridomas that are stable (i.e., hybridomas that maintain the ability to produce a particular antibody for an extended time periods, e.g., at least one year). In other words, a monoclonal-antibody producing hybridoma cell line produced using a subject fusion partner can be subcloned and subcultured for many passages, until sufficient numbers of cells are obtained to produce IgG antibody in amounts ranging from 1 milligram to 20 milligrams. In many embodiments, the hybridoma cell line will be subcloned and subcultured to reach a cell number of 30 million, and further subcultured in a high-density culture system such as the Integra CellLine flask (BD Biosciences). This typically allows the recovery of five to twenty milligrams of IgG antibody from the hybridoma cell supernatant. In particular embodiments, amount of antibody produced after one year of culture will be at least 70%, at least 80%, at least 90%, or, in certain embodiments at least 95% of the amount of antibody produced at the beginning of the year.

Antibody-producing cells suitable for fusion with a subject fusion partner include lymphocyte cells, e.g., a B lymphocyte. In a certain embodiments, spleen cells from a hyperimmunized mammal, e.g., a rabbit, are cultured with the subject fusion partner under conditions which allow the cells to fuse. The hybridoma may be referred to a rabbit-rabbit hybridoma. Such cell fusion methods are described in Spieker-Polet, supra, and, as such, are well known in the art.

Further, and depending on exactly how the subject cell is made, the cell may further contain a recombinant construct (e.g., a retroviral vector inserted into the genome of the cell) adapted for expression of an immortalizing (i.e., transforming) oncogene, i.e., a gene that allows a cell to grow indefinitely in culture. Suitable oncogenes are well known in the art (see, e.g., Katakura, Methods Cell Biol. 1998 57:69-91 for a review). In one exemplary embodiment, the cell may express both the myc and abl oncogenes, although a variety of other oncogenes may be readily employed for the same purpose. Expression of the oncogene in the cell may by directed by an immunoglobulin gene enhancer, e.g., the Eκ or Eμ.

The subject fusion partner may be made by a variety of different methods. In certain embodiments, the subject fusion partner may be made by producing a parental fusion partner using a transgenic rabbit, and then manipulating the parental fusion partner in culture to produce a fusion partner having the desired characteristics. For example, a suitable parent fusion partner may be made using known methods, e.g., those described in Spieker-Polet, supra, and that parental fusion partner may modified by a number of means to produce the subject fusion partner. In one embodiment, the parental fusion partner is a cell line called 240E-1, as described in U.S. Pat. No. 5,675,063 and Spieker-Polet, supra, and deposited at the ATCC as accession no. HB-11870, or a cultured thereof.

In one embodiment and as described in U.S. Pat. No. 5,675,063, a transgenic rabbit is produced that contains a germ line insertion of an oncogenic transgene, and expression of the transgene results in tumor growth. A plasmacytoma (a tumor of B lymphocytes or plasma cells) forms as a result of the tumor growth, and the plasmacytoma may be isolated from the transgenic rabbit and cultured in vitro to produce a parental fusion partner. The plasmacytoma cells may be irradiated in the presence of 8-azaguanine to produce and select HAT sensitive mutants.

In another embodiment, a plasma cell may be isolated from a rabbit and immortalized in culture via introduction of a construct for expressing an oncogene. Such methods are standard in the art and reviewed in Katakura (Methods Cell Biol. 1998 57:69-91).

Once a suitable parental fusion partner is obtained, the parental fusion partner may be modified by a number of different means to produce a subject fusion partner.

In one embodiment, the parent fusion partner may be repeatedly sub-cloned to produce the subject fusion partner. Sub-cloning methods usually involve culturing a population of cells to produce single colonies, plating out cells from those single colonies onto separate plates, and re-growing the plated cells into single colonies. Those single colonies can be picked, tested for a desirable property and again sub-cultured. Such methods are particularly suitable for use with unstable cell lines or cell lines that have been mutagenized. For example, in one embodiment, a parental fusion partner cell line can be plated out to produce single colonies, and the single colonies tested for production of endogenous immunoglobulin heavy chain, by RT-PCR or immunological methods, for example. In certain embodiments, up to about five and in certain embodiments up to about 10 rounds of sub-culturing may be employed.

In another embodiment, a subject fusion partner may be made from a parental fusion partner by making a targeted modification, e.g., a targeted insertion, in the immunoglobulin heavy chain locus in the genome of the fusion partner. Since the sequence of the rabbit germline immunoglobulin locus is available (see, e.g., Ros et al, 2004 Gene 330, 49-59) and several fragments and rearranged versions thereof have been deposited in NCBI's PubMed database, such targeted modifications may be done using standard methods.

Once produced, the subject fusion partner may be used as a fusion partner in any method known in the art. For example, a subject fusion partner may be fused to a rabbit spleen cell to produce a stable hybridoma. In one embodiment, a subject fusion partner may be fused to spleen cells of an immunized rabbit to produce a plurality of hybridomas. Those hybridomas may be screened to select a hybridoma producing a monoclonal antibody of interest, and cultured to produce the antibody, typically in the culture supernatant.

Procedures for immunizing animals are well known in the art as are methods for the screening of hybrodimas and isolation of monoclonal antibodies. For example, such methods are described in Harlow et al, (*Antibodies: A Laboratory Manual*, First Edition (1988) Cold Spring Harbor, N.Y.) and other references cited throughout this disclosure.

The fusion partner cell line designated below as 240E-W2 was deposited under the terms of the Budapest Treaty with the American Type Culture Collection, 10801 University Blvd, Manassas, Va. 20110-2209, USA, on BBBBB BBBBB, 2006 and assigned ATCC Accession No. BBBBBBB.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The examples described below employ the materials and methods described in Spieker-Polet (Proc. Natl. Acad. Sci. 1995 92:9348-52), which reference is incorporated by reference herein in its entirety.

Example 1

In initial experiments, 240E-1 cells were fused with spleen cells obtained from an immunized rabbit. Following HAT medium selection, hybridoma colonies were isolated and tested for antibody production. Several antibody-secreting hybridoma clones were obtained. After expansion and repeated passaging of the hybridoma cell lines, it was found that antibody secretion was greatly diminished in a majority of the clones. Similar results were reported by others (Liguori et al., 2001, supra). Furthermore, after subculturing the 240E-1 cells, their efficiency as a fusion partner decreased. Similarly, Rief et al. (1998), supra, reported a low yield of hybridomas, and only one out of six positive hybridomas persisted after subcloning. The 240E-1 cell line is therefore somewhat unstable, and impractical for routine use.

240E-1 cells were subjected to repeated rounds of subcloning. Subclones were selected for high cloning efficiency and robust growth, as well as for morphological characteristics, such as a bright appearance in phase contrast microscopy and formation of uniform adherent colonies. Selected subclones were further tested for their ability to produce stable hybridomas. After completing four rounds of this subcloning process, a stable line (termed 240E-W) was obtained. The morphological appearance of 240E-W cells differed significantly from the parent 240E-1 cells. 240E-W cells adhered more strongly to the substrate and did not form clumps. Fusion of 240E-W cells with splenocytes of immunized rabbits consistently yielded large numbers of stable hybridomas. In a typical experiment, splenocytes from a rabbit immunized with mouse tumor cells were fused with 240E-W cells at a ratio of 2:1, following the protocol outlined in Spieker-Polet et al., 1995, with the following modification: The cells were plated in 96-well plates, and HAT medium was added 3 days after plating. After two weeks, 60% of the wells contained growing colonies. Of these, 50% produced antibodies that reacted with the immunogen. Upon expansion and subcloning, 80% of the clones grew vigorously and retained antibody production over at least 5 passages. Selected hybridoma clones were subcultured for up to one year without decrease in antibody production. Hybridoma cell lines were exceptionally robust and stable, and could be maintained in confluent wells for several days without loss of viability.

Example 2

The 240E-W cell line and the original 240E-1 cell line, express a significant amount of an endogenous IgG heavy chain (endo-IgH), which is readily detectable at the protein and mRNA level (FIG. 3). The expression of endogenous IgH persists in hybridomas derived from 240E-W, and is often equal to or higher than the expression of the splenocyte-derived IgH (spleno-IgH) comprising the heavy chain of the desired antibody secreted by the hybridoma (FIG. 1). As shown in FIG. 1, endo-IgH and spleno-IgH are, in most cases, readily distinguishable by SDS polyacrylamide gel electrophoresis (SDS-PAGE). The nucleotide sequence and deduced amino acid sequence of endo-IgH was determined (FIG. 2), and the identity of the lower band in FIG. 1 as endo-IgH was confirmed by protein sequencing. Endo-IgH can associate with the splenocyte-derived Ig light chain (spleno-IgL), as demonstrated by the presence of the intact 150 kDa IgG complex on non-reducing SDS-PAGE (data not shown). Therefore, in many cases, hybridomas derived from 240E-W secrete a mixture of endo-IgH/spleno-IgL and spleno-IgH/spleno-IgL. In a subset of hybridoma clones, this may result in a loss of specificity and purity of the hybridoma-derived antibody.

It was also found that a rearranged, potentially active, gene encoding an endogenous kappa light chain (endo-IgL)

is present in the 240E-W cell line, although the product of this gene could not be detected on the mRNA or protein level. However, increased expression of the endo-IgL gene was observed in a subset of 240E-W derived hybridomas. The supernatants of these hybridoma cultures contained both endo-IgL and spleno-IgL, in variable relative amounts (see FIG. 1). The nucleotide sequence of endo-IgL was determined, and the identity of the endo-IgL band shown in FIG. 1 was confirmed by protein sequencing. Thus, it was shown that expression of endo-IgL is undetectable in the 240E-W fusion partner cell line, but is detectable, at variable levels, in a subset of hybridomas derived from 240E-W. This potentially affects antibody purity and specific activity, due to the presence of mixed IgG tetramers containing various combinations of endo-IgH, endo-IgL, spleno IgH, and spleno-IgL.

Example 3

Figure 4:
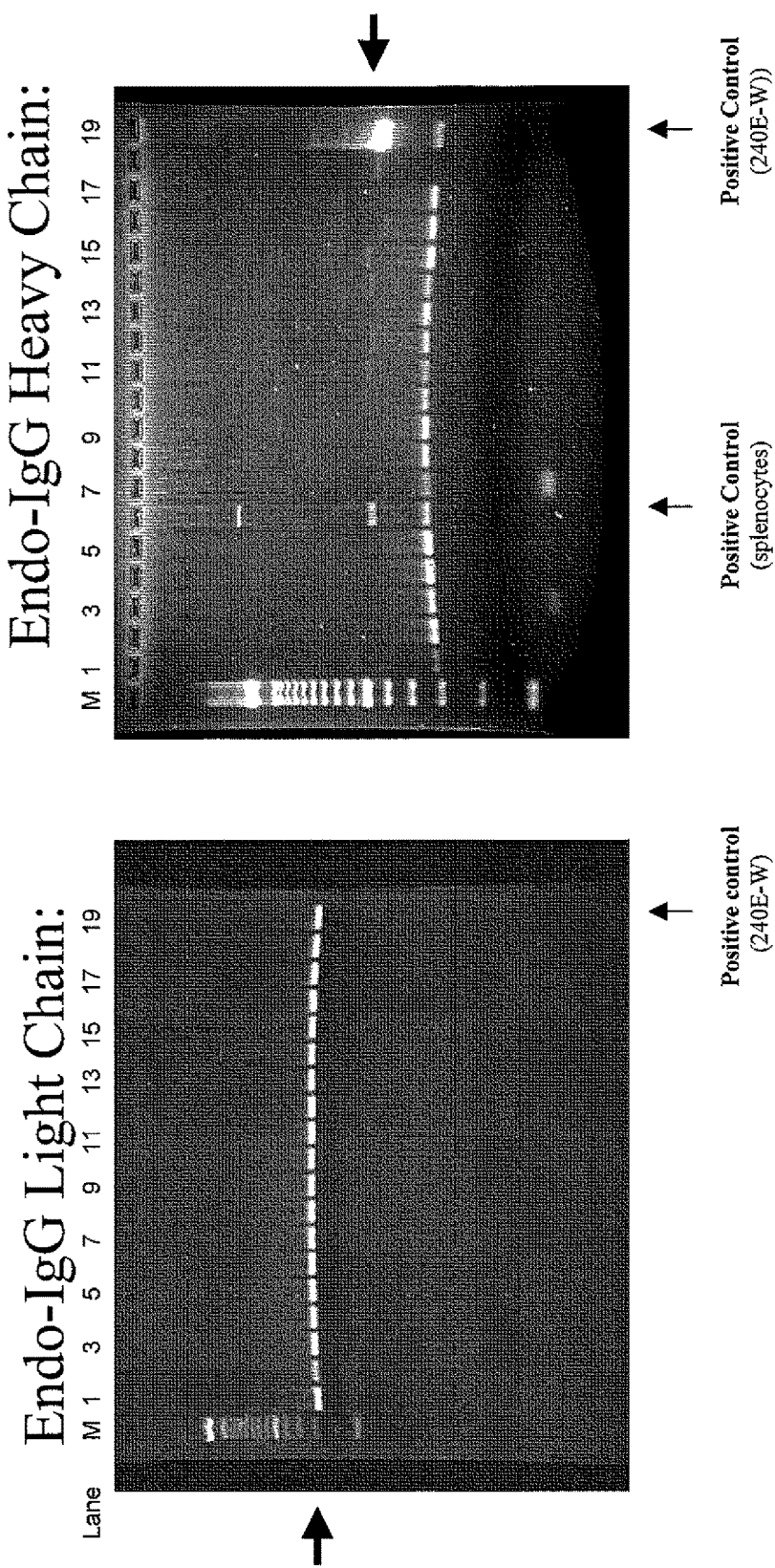
FIG. 4 contains two panels of gels showing genomic PCR amplification products of 240E-W2 clones, and of 240E-W cells. The results show that the gene encoding the endogenous IgH chain is undetectable by genomic PCR in 240E-W2 cells. The 240E-W2 cell line does not contain an intact gene encoding the endogenous Ig heavy chain (endo-IgH). Genomic PCR was performed using primers specific for the gene encoding the endogenous Ig light-chain (left-hand panel), or primers specific for the endo-Ig heavy chain (left-hand panel). DNA was prepared from different 240E-W2 subclones (lanes 1-18), or from the parent cell line, 240E-W (lanes 19). Arrows denote the expected size of the genomic fragment amplified by the primers that were used. Results show that the endo-Ig light chain gene was equally detectable in both 240E-W and 240E-W2, whereas the endo-Ig heavy chain was only detected in 240E-W (lane 19), and in DNA prepared from rabbit splenocytes (lane 6), but not in any of the 240E-W2 clones. Faint bands of variable sizes are likely to represent non-specific amplification products.

Fusion of 240E-W cells with rabbit splenocytes typically yields a subset of hybridoma clones that do not secrete any detectable IgG. Since even in the absence of secreted IgG the cells may contain intracellular IgG heavy chains, several of these clones were tested by immunocytochemistry for the presence of intracellular IgG. Briefly, this was performed by culturing subclones in duplicate 96-well plates, and processing one of the plates for immunocytochemistry by drying, fixation with 0.4% paraformaldehyde, permeabilization with 0.5% Triton X-100, and immunoperoxidase staining with polyclonal goat-anti-rabbit IgG antibodies. Several clones were identified that contained only low levels of IgG, and only in a subset of the cells. One of these hybridoma clones was selected for subcloning and further testing. The cells were grown in standard growth medium ((Spieker-Polet et al., Proc. Natl. Acad. Sci. 1995 92:9348-52), and subcloned by the limiting-dilution method. Single-cell subclones were expanded and again tested for intracellular IgG expression by immunocytochemistry. The subcloning was repeated twice, until a clone was obtained that was 100% IgG-negative. This clone was again subcloned, and it was found that all the subclones remained 100% IgG-negative. In these subclones, IgH mRNA expression was undetectable by RT-PCR. These clones were cultured in the presence of azaguanine (0.13 mM) for 3 weeks to select for revertants that had regained sensitivity to HAT medium selection. Finally, two subclones were selected for further analysis (240E-W2-C2 and 240E-W2-D1). These clones were analyzed by genomic PCR, using primers specific for the endo-IgH sequence. As shown in FIG. 4, the endo-IgH gene was not detected in the 240E-W2 subclones, while it was strongly detected in the 240E-W cell line used as a positive control. In contrast, the endo-IgL gene was equally detectable in 240E-W and 240E-W2 (FIG. 4). This suggests that the 240E-W2 clones have undergone a genetic deletion or rearrangement that resulted in the loss of an intact endo-IgH gene.

The 240E-W2 subclones were further characterized with regard to their utility as a fusion partner. Fusions were performed with splenocytes collected from a rabbit immunized with a peptide derived from human p53 protein, using the fusion partner cell lines 240E-W, 240E-W2-C2, or 240E-W2-D1. The 240E-W2-C2 cell line gave rise to hybridomas that could be selected in HAT medium, and the fusion efficiency (i.e., the percentage of wells containing hybridoma colonies) was higher than the one obtained with 240E-W (82%-100% vs. 64%). In contrast, the 240E-W2-D1 cell line gave rise to hybridomas at a low efficiency (12%-22%). Further, the hybridoma wells derived from 240E-W2-C2 were shown by ELISA to contain antibodies reactive with the immunogen, at a frequency similar to the one observed in the 240E-W fusion. Several of these hybridomas were subcloned and used for in vitro production of antibody, showing that hybridoma clones derived from 240E-W2 and 240E-W are similar in terms of stability and IgG productivity. Taken together, these results demonstrate that the 240E-W2 cell line has the properties expected of an efficient fusion partner for generating rabbit monoclonal antibodies.

Figure 5:
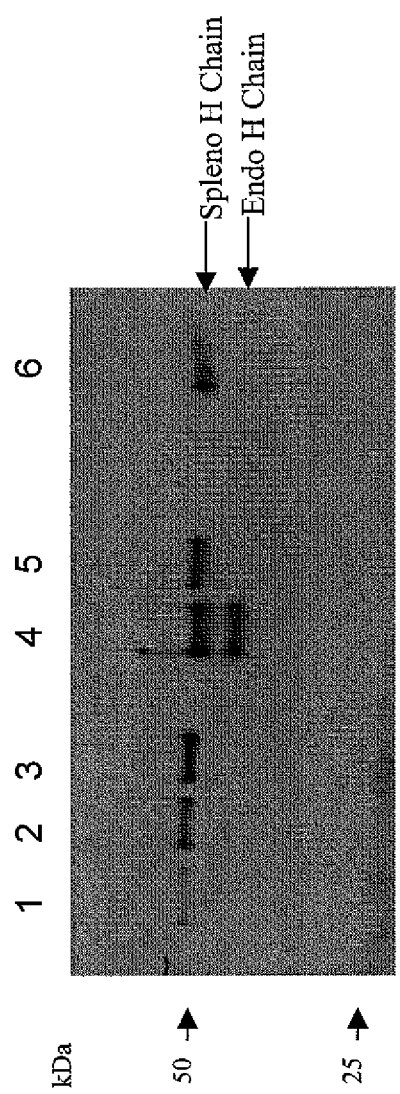
FIG. 5 shows a western blot demonstrating that hybridoma clones derived from 240E-W2-C2 do not secrete any detectable endo-IgH.

SDS-PAGE analysis confirmed that hybridoma clones derived from 240E-W2-C2 do not secrete any detectable endo-IgH (FIG. 5). Expression of endo-IgL was detected in only one of seven hybridoma clones derived from 240E-W2-C2. The removal of endo-IgH is likely to result in improved antibody activity and specificity.

Example 4

Comparative studies were performed to evaluate 240E-W2 with 240E-W. Both 240E-W and 240E-W2 were used as fusion partners to generate hybridomas. Fusions were performed using conventional methodology. $1.5-3 \times 10^8$ lymphocytes from an immunized rabbit and the fusion partner cells were mixed at a ratio of 2:1 with PEG 4000 at (Sigma P7181) 37° C. in serum-free medium. The cells were transferred into 96-well cell culture plates at approximately $1 \times 10^5$ lymphocytes per well in 1640 RPMI medium with 15% FBS (or FCS), incubated in a $CO_2$ incubator. After 48 hr HAT medium (Sigma H0262) was added. Hybridoma colonies were ready for screening in 3-5 weeks. Medium was changed 2-3 times before screening by removing old medium and add fresh medium. Supernatants were tested for the presence of antibody, specific for the immunogen, by ELISA. Western blot analysis was used as a secondary screening assay. The hybridomas were sub-cloned by limit dilution. The fusion partner 240E-W at $2 \times 10^4$ cells per well was used as feeder cells.

ELISA was performed in 96-well micro-titer plates that had been coated overnight with immunogen at 1.0 µg/ml, plates were then saturated with 2% BSA, followed by incubation with the antibody-containing supernatant for 1 hr at room temperature.

After washing with PBS-Tween, alkaline phosphatase conjugated goat anti-rabbit immunoglobulin (IgG) was added and incubation continued for another hour; plates were washed again and developed in the presence of P-NPP (para-nitrophenyl phosphate). Color was read at 405 nm with a plate reader (Multiskan MCC/340 from Fisher Scientific).

Western blot analysis was performed by using whole cell lysates. For example, breast cancer cell line (MCF-7) lysate (50 µg/lane) was loaded on 10% SDS-polyacrylamide gel and proteins were separated by electrophoresis. The proteins on the gel were transferred to nitrocellulose membrane. The blots were blocked with 5% skim milk in phosphate-buffered saline and incubated with the primary antibodies, followed by HRP-conjugated goat anti-rabbit and mouse IgGs (Pierce, 20011). The blots were detected with ECL kit (Amersham RPN2106).

In 53 independent experiments, each for a different antibody, using 240E-W2 as the fusion partner cell, the average fusion efficiency increased by 33%, the positive rates measured by ELISA and Western blot analysis increased by 40% and 24% respectively; and the total success rate for identifying suitable rabbit monoclonal antibodies increases by 41%, as compared with using 240E-W as the fusion partner cell.

A total of 35 hybridomas were subjected large scale production using Integra expression system (DB 353137). In use of these hybridomas, the average antibody yield increased by 32% and specific activities measured by Western blot analysis increased by 133%, compared with hybridomas generated using 240E-W as fusion partner cell.

It is evident from the above results and discussion that the subject invention provides a important new fusion partner for the production of rabbit monoclonal antibodies. Specifically, the subject fusion partner allows highly efficient production of hybridoma cells that are very stable and that produce no antibodies containing heavy chains that are endogenous to the fusion partner. As such, the subject methods and systems find use in a variety of different applications, including research, therapeutic and other applications. The present invention represents a significant contribution to the art.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

---

That which is claimed is:

1. A hybrid cell produced by fusing: i. an antibody-producing cell of a rabbit with ii. a rabbit-derived immortal B-lymphocyte, wherein immunoglobulin heavy chain (IgH) mRNA expression of the rabbit-derived immortal B-lymphocyte is not detectable by RT-PCR and said rabbit-derived immortal B-lymphocyte does not detectably express immunoglobulin heavy chain.

2. The hybrid cell of claim 1, wherein said rabbit is immunized with an antigen.

3. The hybrid cell of claim 2, wherein said hybridoma produces a monoclonal antibody that specifically binds to said antigen.

4. The hybrid cell of claim 1, wherein the antibody-producing cell of a rabbit is a B lymphocyte.

5. The hybrid cell of claim 1, wherein the hybrid cell is immortal.

6. The hybrid cell of claim 1, wherein the rabbit-derived immortal B-lymphocyte does not detectably express immunoglobulin light chain.

7. The hybrid cell of claim 1, wherein the rabbit-derived immortal B-lymphocyte comprises an altered, non-functional, immunoglobulin heavy chain gene.

8. The hybrid cell of claim 1, wherein the rabbit-derived immortal B-lymphocyte comprises a recombinant construct comprising an expression cassette for expressing one or more immortalizing oncogenes.

9. A method of producing a monoclonal antibody comprising:
culturing a hybrid cell produced by fusing: i. an antibody-producing cell of a rabbit with ii. a rabbit-derived immortal B-lymphocyte, wherein immunoglobulin heavy chain (IgH) mRNA expression of the rabbit-derived immortal B-lymphocyte is not detectable by RT-PCR and said rabbit-derived immortal B-lymphocyte does not detectably express immunoglobulin heavy chain,
thereby producing a monoclonal antibody.

10. The method of claim 9, further comprising isolating said monoclonal antibody from said hybridoma cell.

11. The method of claim 9, wherein said rabbit is immunized with an antigen.

12. The method of claim 11, wherein said monoclonal antibody specifically binds to said antigen.

13. The method of claim 11, further comprising producing a modified version of said monoclonal antibody that retains specific binding to said antigen.

14. The method of claim 13, wherein said modified version of said monoclonal antibody is a humanized antibody.

15. The method of claim 9, further comprising testing the monoclonal antibody for binding to an antigen.

16. The method of claim 15, wherein the testing is done by ELISA.

17. The method of claim 9, further comprising amplifying the coding sequences for the heavy and light chain variable domains of the monoclonal antibody from the hybrid cell.

18. The method of claim 17, further comprising producing a recombinant monoclonal antibody using one or more expression cassettes comprising the amplified coding sequences.

19. The method of claim 18, wherein the recombinant monoclonal antibody comprises a heterologous constant region.

20. The method of claim 18, wherein the recombinant monoclonal antibody is a single chain antibody.

* * * * *